United States Patent [19]
Kremer et al.

[11] Patent Number: 6,034,253
[45] Date of Patent: Mar. 7, 2000

[54] PROCESS FOR THE PREPARATION OF 5-(ALKOXYMETHYL)-2,3-PYRIDINEDICARBOXIMIDE COMPOUNDS

[75] Inventors: Kenneth Alfred Martin Kremer; Wen-Xue Wu, both of Lawrenceville; Donald Roy Maulding, deceased, late of Somerville, all of N.J., by Nancy Kay Maulding, executrix

[73] Assignee: America Cyanamid Company, Madison, N.J.

[21] Appl. No.: 09/235,689

[22] Filed: Jan. 22, 1999

Related U.S. Application Data

[62] Division of application No. 08/872,567, Jun. 10, 1997, Pat. No. 5,905,154
[60] Provisional application No. 60/019,510, Jun. 10, 1996.

[51] Int. Cl.[7] .............................................. C07D 207/273
[52] U.S. Cl. ............................................ 548/539; 548/540
[58] Field of Search ..................................... 548/539, 540

[56] References Cited

U.S. PATENT DOCUMENTS

| | | |
|---|---|---|
| 4,353,734 | 10/1982 | Seres et al. . |
| 4,748,244 | 5/1988 | Waldner et al. . |
| 4,754,033 | 6/1988 | Waldner . |
| 5,177,266 | 1/1993 | Strong . |
| 5,288,866 | 2/1994 | Strong . |
| 5,334,576 | 8/1994 | Doehner, Jr. et al. . |
| 5,771,744 | 11/1996 | Hamprecht et al. . |

FOREIGN PATENT DOCUMENTS

| | | |
|---|---|---|
| 0 041 623 | 12/1981 | European Pat. Off. . |
| 0 205 879 | 5/1986 | European Pat. Off. . |
| 0 308 084-A1 | 8/1988 | European Pat. Off. . |

OTHER PUBLICATIONS

Chem. Abst. 98: 107108a, No. 13, Mar. 28, 1983 (Lulukyan, K.K.

M. Kucharski and R. Lubczak, *Acylation of Cyclic Imides*, Chem. Stosow., 1987 31(4) 59–28 (English Abstract).

A. Waldner, Helvetica Chimica Acta, (1988), 71, No. 2, pp. 486–492 (Chem. Abs. 110:23756(e).

*Primary Examiner*—Patricia L. Morris
*Attorney, Agent, or Firm*—Barbara L. Renda

[57] ABSTRACT

There is provided a process for the preparation of 5-(alkoxymethyl)-2,3-pyridinedicarboximide compounds having the structural formula I

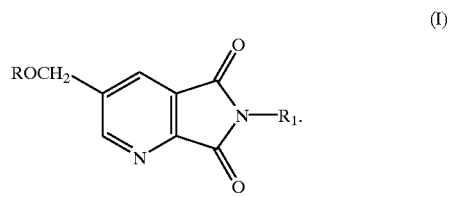

The 5-(alkoxymethyl)-2,3-pyridinedicarboximide compounds are useful as intermediates in the preparation of herbicidal 5-(alkoxymethyl)-2-(2-imidazolin-2-yl)-nicotinic acid, ester and salt compounds.

3 Claims, No Drawings

PROCESS FOR THE PREPARATION OF 5-(ALKOXYMETHYL)-2,3-PYRIDINEDICARBOXIMIDE COMPOUNDS

This is a divisional of application Ser. No. 08/872,567 filed on Jun. 10, 1997, now U.S. Pat. No. 5,905,154 the entire disclosure of which is hereby incorporated by reference. This application claims priority from provisional application, Ser. No. 60/019,510, filed Jun. 10, 1996.

BACKGROUND OF THE INVENTION 5-(Alkoxymethyl)-2,3-pyridinedicarboximide compounds are useful as intermediates in the preparation of herbicidal 5-(alkoxymethyl)-2-(2-imidazolin-2-yl)nicotinic acid, ester and salt compounds. Methods for the preparation of 5-(alkoxymethyl)-2,3-pyridinedicarboximide compounds are rather limited, and those methods that are available may require extensive purification methods to provide high purity 5-(alkoxymethyl)-2,3-pyridinedicarboximide compounds.

European patent application number 308,084-A1 generically discloses that a 5-(alkoxymethyl)-2,3-pyridinedicarboximide compound may be prepared by reacting a substituted oxime compound with a halomaleimide compound optionally in the presence of an inorganic base. However, that method is not satisfactory because it produces a mixture that contains the desired 5-(alkoxymethyl)-2,3-pyridinedicarboximide compound and a relatively high percentage of an undesirable 5-methyl-2,3-pyridinedicarboximide compound. Arduous or time consuming purification methods are then required to obtain high purity 5-(alkoxymethyl)-2,3-pyridinedicarboximide compounds. If the mixture is not highly purified, the 5-(alkoxymethyl)-2-(2-imidazolin-2-yl)nicotinic acid, ester or salt compound prepared from the mixture will be contaminated with a 5-methyl-2-(2imidazolin-2-yl)nicotinic acid, ester or salt compound which has different herbicidal properties than the desired compound.

It is, therefore, an object of the present invention to provide a process for the preparation of high purity 5-(alkoxymethyl)-2,3-pyridinedicarboximide compounds.

SUMMARY OF THE INVENTION

The present invention provides an effective and efficient process for the preparation of a 5-(alkoxymethyl)-2,3-pyridinedicarboximide compound having the structural formula I

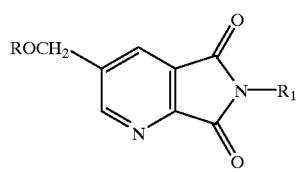

(I)

wherein
R is $C_1$–$C_6$alkyl;
$R_1$ is hydrogen, $C_1$–$C_6$alkyl, $C(O)R_2$,
  phenyl optionally substituted with any combination of from one to four halogen, $C_1$–$C_4$alkyl, $C_1$–$C_4$alkoxy, nitro or cyano groups,
  benzyl optionally substituted on the phenyl ring with any combination of from one to four halogen, $C_1$–$C_4$alkyl, $C_1$–$C_4$alkoxy, nitro or cyano groups, or

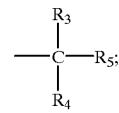

$R_2$ is $C_1$–$C_6$alkyl,
  phenyl optionally substituted with any combination of from one to four halogen, $C_1$–$C_4$alkyl, $C_1$–$C_4$alkoxy, nitro or cyano groups, or
  benzyl optionally substituted on the phenyl ring with any combination of from one to Four halogen, $C_1$–$C_4$alkyl, $C_1$–$C_4$alkoxy, nitro or cyano groups;
$R_3$ and $R_4$ are each independently $C_1$–$C_4$alkyl; and
$R_5$ is cyano or $CONH_2$,
which process comprises reacting an oxime of a 2-(alkoxymethyl)-2-propen-1-one compound having the structural formula II

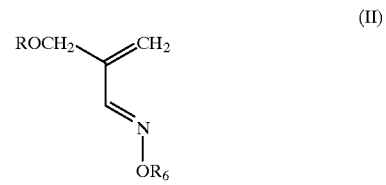

(II)

wherein R is as described above and $R_6$ is hydrogen or $C_1$–$C_6$alkyl with a substituted maleimide compound having the structural formula III

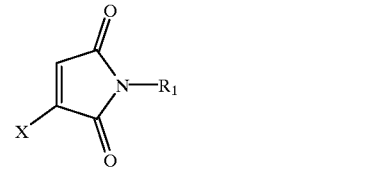

(III)

wherein $R_1$ is as described above and X is halogen, phenylsulfinyl or 1-imidazolyl and a base selected from the group consisting of tri($C_2$–$C_4$alkyl)amine, an alkali metal acetate and mixtures thereof in the presence of a solvent at an elevated temperature.

Surprisingly, it has been found that 5-(alkoxymethyl)-2,3-pyridinedicarboximide compounds are obtained in high purity when prepared by the effective and efficient process of the present invention.

DETAILED DESCRIPTION OF THE INVENTION

In one preferred embodiment of the present invention, an oxime of a 2-(alkoxymethyl)-2-propen-1-one compound represented by formula II is reacted with at least about one molar equivalent of a substituted maleimide compound represented by formula III, and at least about one molar equivalent of a tri($C_2$–$C_4$alkyl)amine or an alkali metal acetate or a mixture thereof, preferably in a temperature range of about 75° C. to 150° C., more preferably about 90° C. to 135° C., in the presence of a solvent having a boiling point of at least about 75° C.

Advantageously, it has now been found that 5-(alkoxymethyl)-2,3-pyridinedicarboximide compounds are obtained in high purity by the effective and efficient process of the present invention. In contrast, 5-(alkoxymethyl)-2,3-pyridinedicarboximide compounds are contaminated with significant amounts of 5-methyl-2,3-pyridinedicarboximide compounds when prepared according to the procedure described in EP 308,084-A1.

The 5-(alkoxymethyl)-2,3-pyridinedicarboximide compounds may be isolated by diluting the reaction mixture with water and filtering the formula I product from the aqueous mixture. The product formula I compounds may also be Isolated by concentrating the reaction mixture in vacuo and filtering the formula I product from the concentrated mixture. Alternatively, the reaction mixture may be integrated into the process used to prepare the final herbicidal agent without isolating the formula I compound.

Exemplary of halogen hereinabove are fluorine, chlorine, bromine and iodine.

The base is an especially important element of the present invention because it significantly reduces the production of 5-methyl-2,3-pyridinedicarboximide compounds. Tri($C_2$–$C_4$alkyl)amines suitable for use in the process of the present invention include triethylamine, N,N-diethylisopropylamine, N,N-diisopropyiethylamine and the like with triethylamine being preferred. Alkali metal acetates suitable for use in the process of this invention include sodium acetate, potassium acetate and the like with sodium acetate and potassium acetate being preferred.

In another preferred embodiment of The present invention, a phase transfer catalyst is present. Preferably, the phase transfer catalyst is present when the alkali metal acetate is present. Phase transfer catalysts suitable for use in the present invention include any conventional phase transfer catalysts. Preferred phase transfer catalysts include crown ethers such as 18-crown-6 and 15-crown-5.

Solvents suitable for use in the process of the present invention preferably have a boiling point of at least about 75° C. and include aromatic hydrocarbons such as toluene, xylenes, mesitylene and mixtures thereof; halogenated aromatic hydrocarbons such as mono- and dihalobenzenes and mixtures thereof; polynuclear aromatic hydrocarbons such as naphthalene, alkylnaphthalenes and mixtures thereof; glycols such as 1,2-diethoxyethane and mixtures thereof; and mixtures thereof. Preferred solvents include toluene, xylenes, mesitylene, 1,2-diethoxyethane and mixtures thereof with toluene being more preferred.

In another embodiment of the present invention, an alkali metal carbonate such as sodium carbonate, potassium carbonate and the like is present. Preferably, the alkali metal carbonate is present when the tri-($C_2$–$C_4$alkyl)amine is present.

The process of the present invention is especially useful for the preparation of 5-(alkoxymethyl)-2,3-pyridinedicarboximide compounds wherein R is methyl; and
$R_1$ is methyl, phenyl or

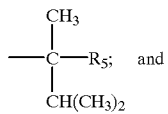 and $R_5$ is cyano or $CONH_2$.

Oximes of 2-(alkoxymethyl)-2-propen-1-one compounds and substituted maleimide compounds which are particularly useful in the process of this invention are those wherein R and $R_6$ are methyl;

$R_1$ is methyl, phenyl or

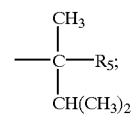

$R_5$ is cyano or $CONH_2$; and
X is Cl or Br.

The formula II oxime compounds of the present invention may be prepared by reacting a 2-alkoxymethyl-acrolein of formula IV with a substituted hydroxylamine of formula V optionally in the presence of a base. The reaction is shown below in Flow Diagram I.

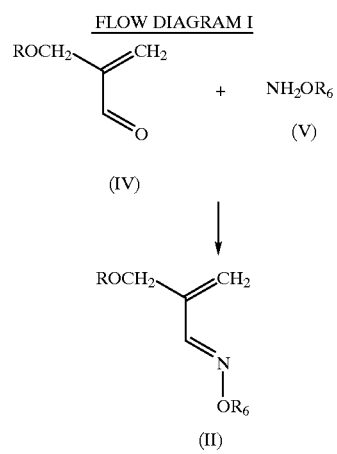

Alternatively, oxime compounds of formula II wherein $R_6$ is $C_1$–$C_6$alkyl may be prepared by reacting a formula II compound wherein $R_6$ is hydrogen with a dialkyl sulfate of formula VI and a base such as sodium hydroxide or an alkali metal alkoxide optionally in the presence of a phase transfer catalyst. The reaction scheme is shown in Flow Diagram II.

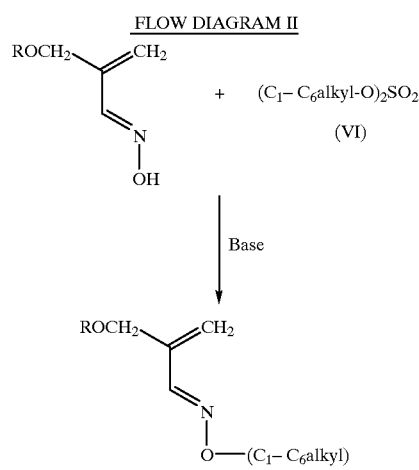

A method for the preparation of formula IV 2-alkoxymethylacroleins is described in U.S. Pat. No. 5,177, 266. Formula III substituted maleimide compounds wherein X is halogen and $R_1$ is hydrogen, $C_1$–$C_6$alkyl, phenyl, substituted phenyl, benzyl, substituted benzyl or —$CR_3R_4R_5$ are known in the art and may be prepared according to the procedures described in EP 308,084-A1.

Substituted maleimide compounds wherein $R_1$ is $C(O)R_2$ may be prepared by reacting a formula III compound wherein $R_1$ is hydrogen with an acid chloride of formula VI in the presence of a solvent as shown in Flow Diagram III.

FLOW DIAGRAM III

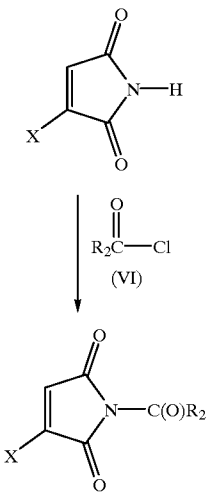

Formula III compounds wherein X is 1-imidazolyl may be prepared by reacting a formula III compound wherein X is Cl or Br with imidazole and a base such as a tri($C_1$–$C_4$alkyl) amine in the presence of a solvent. And formula III compounds wherein X is phenylsulfinyl may be prepared by reacting a formula III compound wherein X is Cl or Br with thiophenol and a base such as an alkali metal acetate in the presence of a solvent to form an intermediate compound and oxidizing the intermediate compound with a conventional oxidizing agent in the presence of a solvent to form the desired formula III compound wherein X is phenylsulfinyl.

The present invention also provides a process for the preparation of a herbicidal 5-(alkoxymethyl)-2-(2-imidazolin-2-yl)-nicotinic acid, ester and salt compound having the formula

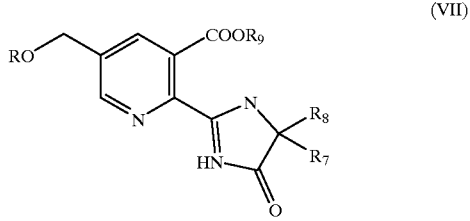

(VII)

wherein
R is as defined above;
$R_7$ is $C_1$–$C_4$ alkyl;
$R_8$ is $C_1$–$C_4$ alkyl, $C_3$–$C_6$ cycloalkyl or $R_7$ and $R_8$ when taken together with the atom to which they are attached, represent a $C_3$–$C_6$ cycloalkyl group optionally substituted with methyl and
$R_9$ is hydrogen, diloweralkylinmino,
$C_1$–$C_{12}$ alkyl optionally substituted with one of the following groups: $C_1$–$C_3$ alkoxy, halogen, hydroxy, $C_3$–$C_6$ cycloalkyl, benzyloxy, furyl, phenyl, halophenyl, lower alkylphenyl, lower alkoxyphenyl, nitrophenyl, carboxyl, loweralkoxycarbonyl, cyano or triloweralkylammonium;
$C_3$–$C_{12}$ alkenyl optionally substituted with one of the following groups: $C_1$–$C_3$ alkoxy, phenyl, halogen or loweralkoxycarbonyl or with two $C_1$–$C_3$ alkoxy groups or two halogen groups;

$C_3$–$C_6$ cycloalkyl optionally substituted with one or two $C_1$–$C_3$ alkyl groups;
or a cation preferably selected from the group consisting of alkali metals, alkaline earth metals, manganese, copper, iron, zinc, cobalt, lead, silver, nickel, ammonium and organic ammonium;

which process comprises:

(a) preparing a compound having the formula I

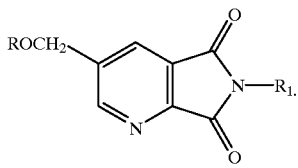

(I)

wherein R and $R_1$ are as defined above by a process as defined above; and (b) converting the said compound having formula I into the compound having the formula VII.

The term "lower" as used above in relation to alkyl and alkoxy groups means that the alkyl or alkoxy group contains 1 to 6, preferably 1 to 4, carbon atoms.

The conversion of the compound having formula I into the compound having formula VII may be carried out in a variety of ways. One may plan routes by combining reactions known for the conversion of one carboxylic acid derivative into another.

Methods that may be used to create the imidazolinone herbicides are illustrated in the book "The Imidazolinone Herbicides" edited by D. L. Shaner and S. L. O'Connor, published 1991 by CRC Press, Boca Raton, Florida with particular reference to Chapter 2 entitled "Synthesis of the Imidazolinone Herbicides", pages 8–14 and the references cited therein. The following patent literature references also illustrate the methods that may be used to convert the carboxylic acid derivatives into imidazolinone final products:

U.S. Pat. Nos. 5,371.229; 5,334,576; 5,250,694; 5,276,157; 5,110,930: 5,122,608; 5,206,368; 4,925,944; 4,921.961; 4,959,476; 5,103,009; 4,816,588; 4,748,244; 4,754,033; 4,757,146; 4,798,619; 4,766,218; 5,001,254; 5,021,078; 4,723,011; 4,709,036; 4,658,030; 4,608,079; 4,719,303; 4,562,257; 4,459,408; 4,459.409; 4,460,776; 4,125,727 and 4,758,667, and European Patent Application Nos. EP-A-0-041,623 and EP-A-0-308,084.

In order to facilitate a further understanding of the invention, the following examples are Presented primarily for the purpose of illustrating more specific details thereof. The Invention should not be deemed limited by the examples as the full scope of the invention is defined in the claims.

EXAMPLE 1

Preparation of 5-(Methoxymethyl)-N-phenyl-2,3-pyridinedicarboximide

EXAMPLE 1

Preparation of 5-(Methoxymethyl)-N-phenyl-2,3-pyridinedicarboximide

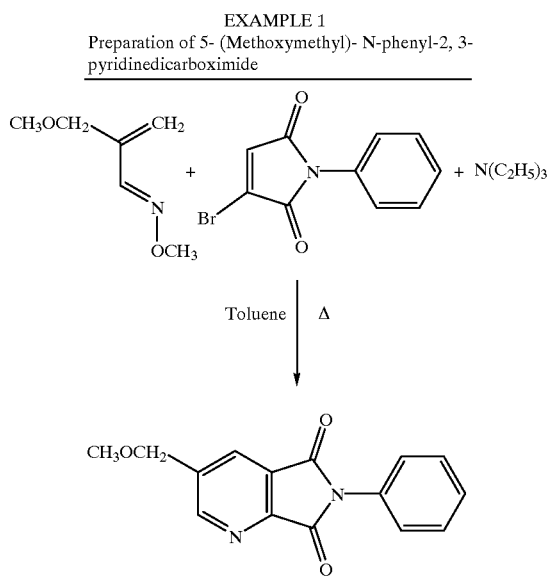

A solution of the O-methyloxime of 2-(methoxymethyl)-2-propen-1-one (9.0 g, 96% pure, 67 mmol) in toluene (112 g) is heated at 97° C. for 27 hours. During the heating period, 2-bromo-N-phenylmaleimide (27.75 g, 110 mmol) and triethylamine (17.9 g, 177 mmol) are added portionwise to the reaction mixture. The final reaction mixture is filtered to remove solids, washed with water and concentrated in vacuo to give the title product as an orange solid (10.9 g, 61% yield) having a 5-(methoxymethyl)-N-phenyl-2,3-pyridinedicarboximide to 5-methyl-N-phenyl-2,3-pyridinedicarboximide ratio of 233:1.

EXAMPLES 2–9

The procedure of Example 1 is repeated using a variety of conditions and the results are summarized in Table I.

As can be seen from the data in Examples 1–9, the process of the present invention (Examples 1–7) produces 5-(methoxymethyl)-N-phenyl-2,3-pyridinedicarboximide which is contaminated with a significantly smaller amount of 5-methyl-N-phenyl-2,3-pyridinedicarboximide than the process described in EP 308,084-A1 (Examples 8 and 9).

TABLE I

Preparation of 5-(Methoxymethyl)-N-phenyl-2,3-pyridinedicarboximide

| Example | Eq. of 2-bromo-N-phenyl-maleimide | Base/Eq. | Eq. of 18-Crown-6 | Solvent | Temp. (° C.) | Time (hrs) | % Yield[1] | Ratio[2] |
|---|---|---|---|---|---|---|---|---|
| 2 | 1.3 | $N(C_2H_5)_3$/3 | — | toluene | reflux | 23 | 51 | 180:1 |
| 3 | 1.2 | NaOAc/7 | — | 1,2-diethoxyethane | 100 | 35 | 44 | 30:1 |
| 4 | 2.0 | $Na_2CO_3$/3.1 | — | toluene | reflux | 34 | 62 | 179:1 |
| 5 | 2.7 | $N(C_2H_5)_3$/1 KOAc/4.2 | 0.1 | toluene | reflux | 37 | 52 | 54:1 |
| 6 | 2.2 | $(CH_3)_2CHNC_2H_5$/3.1 | — | toluene | 100 | 33 | 31 | 28:1 |
| 7 | 1.0 | NaOAc/5 | — | toluene | 95 | 28 | 47 | 28:1 |
| 8 | 1.0 | $K_2CO_3$/7.3 | — | toluene | reflux | 22 | 31 | 1:1 |
| 9 | 1.0 | $K_2CO_3$/1.8 | — | toluene | 98 | 19 | 44 | 4:1 |

[1]Determined by GC analysis of reaction mixture.
[2]Ratio of 5-(methoxymethyl)-N-phenyl-2,3-pyridinedicarboximide to 5-methyl-N-phenyl-2,3-pyridinedicarboximide.

EXAMPLES 10–12

Using essentially the same procedure as described in Example 1. but substituting 2-chloro-N-phenylmaleimide for 2-bromo-N-phenylmaleimide, 5-methoxymethyl-N-phenyl-2,3-pyridinedicarboximide is produced in the yields shown in Table II.

TABLE II

Preparation of 5-(Methoxymethyl)-N-phenyl-2,3-pyridinedicarboximide

| Example | Eq. of 2-chloro-N-phenylmaleimide | Base/Eq. | Eq. of 18-Crown-6 | Solvent | Temp. (° C.) | Time (hrs) | % Yield[1] | Ratio[2] |
|---|---|---|---|---|---|---|---|---|
| 10 | 1.7 | $N(C_2H_5)_3$/2.7 | — | toluene | 95 | 43 | 59 | 224:1 |
| 11 | 3.0 | KOAc/4.1 | 0.05 | toluene | reflux | 37 | 70 | 45:1 |
| 12 | 1.1 | NaOAc/4.5 | — | toluene | 90 | 55 | 59 | 68:1 |

[1]Determined by GC analysis of reaction mixture.
[2]Ratio of 5-(methoxymethyl)-N-phenyl-2,3-pyridinedicarboximide to 5-methyl-N-phenyl-2,3-pyridinedicarboximide.

EXAMPLE 13

Preparation of 5-(Methoxymethyl)-N-methyl-2,3-pyridinedicarboximide

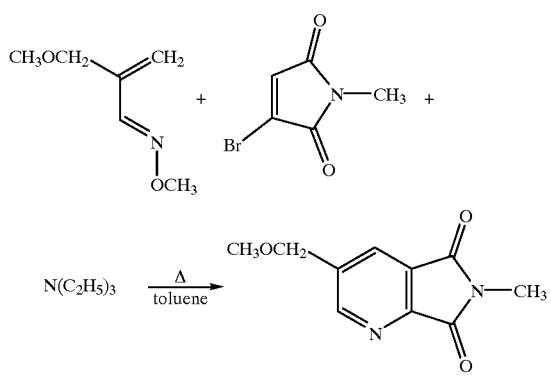

A solution of O-methyloxime of 2-(methoxymethyl)-2-propen-1-one (9.9 g, 84% pure, 64 mmol) in toluene (112 g) is heated at 100° C. for 44 hours. During the heating period, 2-bromo-N-methylmaleimide (20.35 g, 107 mmol) and triethylamine (16.9 g, 167 mmol; are added portionwise to the reaction mixture. The final reaction mixture is filtered to remove solids, washed with water and concentrated in vacuo to give the title product as an orange solid (8.1 g, 61% yield) having a 5-(methoxymethyl)-N-methyl-2,3-pyridinedicarboximide to 5-methyl-N-methyl-2,3-pyridinedicarboximide ratio of 316:1.

EXAMPLES 14 AND 15

Using essentially the same procedure as described in Example 13, 5-(methoxymethyl)-N-methyl-2,3-pyridinedicarboximide is produced in the yields shown in Table III.

TABLE III

Preparation of 5-(Methoxymethyl)-N-methyl-2,3-pyridinedicarboximide

| Example | Eq. of 2-bromo-N-methylmaleimide | Base/Eq. | Eq. of 18-Crown-6 | Solvent | Temp. (° C.) | Time (hrs) | % Yield[1] | Ratio[2] |
|---|---|---|---|---|---|---|---|---|
| 14 | 1.0 | NaOAc/6.5 | — | toluene | 100 | 44 | 60 | 70:1 |
| 15 | 2.4 | KOAc/4.1 | 0.01 | toluene | reflux | 30 | 52 | 175:1 |

[1]Determined by GC analysis of reaction mixture.
[2]Ratio of 5-(methoxymethyl)-N-phenyl-2,3-pyridinedicarboximide to 5-methyl-N-phenyl-2,3-pyridinedicarboximide.

EXAMPLES 16–18

Using essentially the same procedure as described in Example 13, but substituting 2-chloro-N-methylmaleimide for 2-bromo-N-methylmaleimide, 5-(methoxymethyl)-N-methyl-2,3-pyridinedicarboximide is produced in the yields shown in Table IV.

TABLE IV

Preparation of 5-(Methoxymethyl)-N-methyl-2,3-pyridinedicarboximide

| Example | Eq. of 2-chloro-N-methylmaleimide | Base/Eq. | Eq. of 18-Crown-6 | Solvent | Temp. (° C.) | Time (hrs) | % Yield[1] | Ratio[2] |
|---|---|---|---|---|---|---|---|---|
| 16 | 1.3 | $Na_2CO_3$/3.1 $N(C_2H_5)_3$/1 | — | toluene | reflux | 29 | 51 | 166:1 |
| 17 | 1.6 | KOAc/4.2 | 0.01 | toluene | reflux | 33 | 50 | 110:1 |
| 18 | 1.5 | $N(C_2H_5)_3$/2.7 | — | toluene | 100 | 40 | 65 | 177:1 |

[1]Determined by GC analysis of reaction mixture.
[2]Ratio of 5-(methoxymethyl)-N-phenyl-2,3-pyridinedicarboximide to 5-methyl-N-phenyl-2,3-pyridinedicarboximide.

EXAMPLE 19

Preparation of 5,7-Dihydro-α-isopropyl-3-(methoxymethyl)-α-methyl-5,7-dioxo-6H-pyrrolo[3,4-b]pyridine-6-acetonitrile

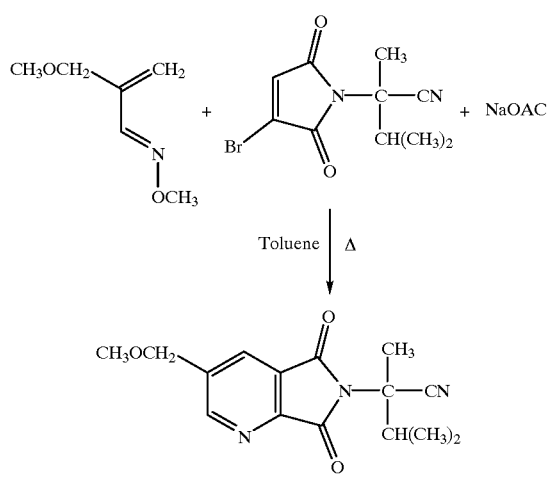

A mixture of 3-bromo-2,5-dihydro-α-isopropyl-α-methyl-2,5-dioxopyrrole-1-acetonitrile (0.6 g, 90% pure, 1.99 mmol) in toluene (12 g) is heated at 95° C. for 41 hours. During the heating period, the O-methyloxime of 2-(methoxymethyl)-2-propen-1-one (0.27g, 2.0 mmol) and sodium acetate (0.76 g, 9.2 mmol) are added portionwise to the reaction mixture. The final reaction mixture is filtered to remove solids, washed with water and concentrated in vacuo to give the title product as a red oil (0.40 g, 70% yield) having a 5,7-dihydro-α-isopropyl-3-(methoxymethyl)-α-methyl-5,7-dioxo-6H-pyrrolo[3,4-b]pyridine-6-acetonitrile to 5,7-dihydro-α-isopropyl- 3,α-dimethyl-5,7-dioxo-6H-pyrrolo[3,4-b]pyridine-6-acetonitrile ratio of 61:1.

Using essentially the same procedure, but in the absence of a base, 5,7-dihydro-α-isopropyl-3-(methoxymethyl)-α-methyl-5,7-dioxo-6H-pyrrolo[3,4-b]pyridine-6-acetonitrile is obtained in 32% yield with a 5,7-dihydro-α-isopropyl-3-(methoxymethyl)-α-methyl-5,7-dioxo-6H-pyrrolo[3,4-b]pyridine-6-acetonitrile to 5,7-dihydro-α-isopropyl-3,α-dimethyl-5,7-dioxo-6H-pyrrolo[3,4-b]pyridine-6-acetonitrile ratio of 2:1.

EXAMPLE 20

Preparation of the Oxime of 2-(methoxymethyl)-2-propen-1-one

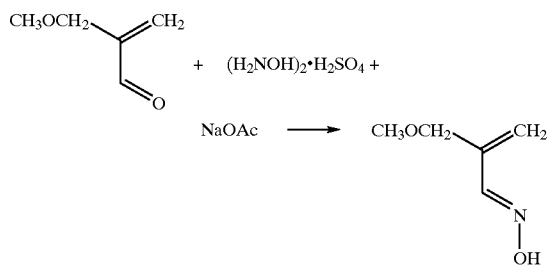

A mixture of hydroxylamine sulfate (3.81 g, 23.2 mmol) and sodium acetate (3.52 g, 4.29 mmol) in water (30 g) is treated dropwise with 2-methoxymethylacrolein (5.1 g, 70% pure) over 15 minutes, stirred at room temperature for 5 hours and extracted with methylene chloride. The organic extract is dried over anhydrous magnesium sulfate and concentrated in vacuo to give the title product as a yellow oil (3.3 g, 80% yield).

EXAMPLE 21

Preparation of the O-methyloxime of 2-(methoxymethyl)-2-propen-1-one

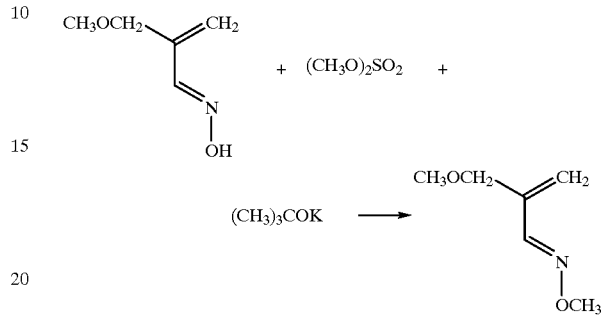

A mixture of the oxime of 2-(methoxymethyl)-2-propen-1-one (1.8 g, 10.4 mmol, 67% pure) and potassium tert-butoxide (1.93 g, 17.2 mmol) in tetrahydrofuran (40 g) is stirred at 5° to 10° C. for 10 minutes, treated dropwise with dimethyl sulfate (2.37 g, 18.8 mmol), stirred for 1.2 hours, filtered to remove solids and concentrate in vacuo to obtain a residue. The residue is dissolved in methylene chloride and the resultant solution is washed sequentially with water and brine, dried over anhydrous magnesium sulfate and concentrated in vacuo to give the title product as a yellow oil (1.4 g, 74% yield).

EXAMPLE 22

Preparation of the O-methyloxime of 2-(methoxymethyl)-2-propen-1-one

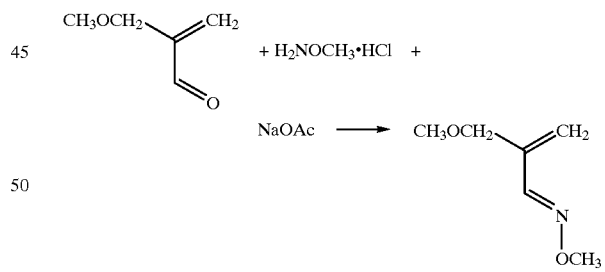

A mixture of methoxylamine hydrochloride (21.0 g, 0.25 mol) and sodium acetate 22.4 g, 0.27 mol) in water (159 g) is created dropwise with 2-methoxymethylacrolein (21.0 g, 90% pure, 0.19 mol) over ten minutes at 21° to 29° C., stirred overnight at room temperature and extracted with methylene chloride. The organic extract is washed sequentially with water and brine, dried over anhydrous magnesium sulfate and concentrated in vacuo to give the title product as a yellow oil (26.1 g). A portion of the yellow oil is distilled under reduced pressure (50° to 70° C., 16 mm Hg) to give the title product as a clear, colorless oil.

We claim:
1. A compound having the structural formula

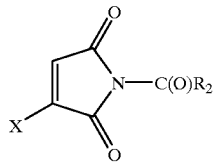

wherein
X is halogen; and $R_2$ is $C_1$–$C_6$alkyl,
  phenyl optionally substituted with any combination of from one to four halogen, $C_1$–$C_4$alkyl, $C_1$–$C_4$alkoxy, nitro or cyano groups, or
  benzyl optionally substituted on the phenyl ring with any combination of from one to four halogen, $C_1$–$C_4$alkyl, $C_1$–$C_4$alkoxy, nitro or cyano groups.

2. The compound according to claim 1 wherein X is Cl or Br.

3. The compound according to claim 2 wherein $R_2$ is $C_1$–$C_4$alkyl, phenyl or benzyl.

* * * * *